US010299965B1

(12) United States Patent
Brar (10) Patent No.: US 10,299,965 B1
(45) Date of Patent: May 28, 2019

(54) ANTIMICROBIAL DEVICE FOR WOUND CARE

(71) Applicant: Harjeet S. Brar, Bakersfield, CA (US)

(72) Inventor: Harjeet S. Brar, Bakersfield, CA (US)

(*) Notice: Subject to any disclaimer, the term of this patent is extended or adjusted under 35 U.S.C. 154(b) by 0 days.

(21) Appl. No.: 14/717,936

(22) Filed: May 20, 2015

(51) Int. Cl.
| | |
|---|---|
| *A61M 1/00* | (2006.01) |
| *A61F 13/00* | (2006.01) |
| *A61F 13/02* | (2006.01) |
| *A61M 35/00* | (2006.01) |
| *A61M 37/00* | (2006.01) |

(52) U.S. Cl.
CPC .... *A61F 13/0203* (2013.01); *A61F 13/00063* (2013.01); *A61F 13/00068* (2013.01); *A61M 1/0019* (2013.01); *A61M 1/0088* (2013.01); *A61M 35/00* (2013.01); *A61M 37/0092* (2013.01); *A61F 2013/00174* (2013.01); *A61M 2202/0007* (2013.01); *A61M 2202/02* (2013.01); *A61M 2205/0205* (2013.01); *A61M 2205/36* (2013.01); *A61M 2210/04* (2013.01)

(58) Field of Classification Search
CPC ...... A61M 5/14248; A61M 2005/3022; A61M 1/0019; A61M 1/0088; A61M 35/00; A61M 37/0092; A61M 2202/0007; A61M 2202/02; A61M 2205/0205; A61M 2205/36; A61M 2210/04; A61F 35/006; A61F 13/0203; A61F 13/00063; A61F 13/00068; A61F 2013/00174
See application file for complete search history.

(56) References Cited

U.S. PATENT DOCUMENTS

| | | | |
|---|---|---|---|
| 4,475,900 A | 10/1984 | Popovich et al. | |
| 5,334,166 A | 8/1994 | Palestrant | |
| 5,620,424 A | 4/1997 | Abramson | |
| 5,695,482 A | 12/1997 | Kaldany | |
| 6,461,569 B1 | 10/2002 | Boudreaux | |
| 7,947,021 B2 | 5/2011 | Bourne et al. | |
| 2007/0167926 A1* | 7/2007 | Blott | A61F 13/0213 604/304 |
| 2008/0051736 A1 | 2/2008 | Rioux et al. | |
| 2009/0306609 A1* | 12/2009 | Blott | A61M 1/0037 604/305 |
| 2010/0106103 A1 | 4/2010 | Ziebol et al. | |
| 2011/0004171 A1* | 1/2011 | Blott | A61M 1/0088 604/305 |

(Continued)

OTHER PUBLICATIONS

Haaland, Carter, "Fellows invent UV catheter sleeve," mndaily.com, Sep. 22, 2009 (US).

(Continued)

*Primary Examiner* — Lauren P Farrar
(74) *Attorney, Agent, or Firm* — R. Scott Kimsey, Esq.; Klein DeNatale Goldner (57) ABSTRACT

A device for protecting against microbial infection includes a cover having a concave interior surface and a convex exterior surface. The device further includes an adhesive flange for affixing the cover to a patient's skin. A membrane extends across at least a portion of the interior surface of the cover for retaining an antimicrobial compound between the membrane and the interior surface of the cover. The membrane is permeable to the antimicrobial compound so that the antimicrobial compound is released through the membrane over time.

9 Claims, 7 Drawing Sheets

(56) References Cited

U.S. PATENT DOCUMENTS

2011/0213339 A1    9/2011    Bak

OTHER PUBLICATIONS

Author Unknown, "Medical device infection control system for sterilization of catheter access point with ultraviolet light," Regents of the Univ. of Minnesota, Jun. 25, 2010, US.
Author Unknown, "Ultra-Clean Catheter Site Disinfection System," UVSolutions, Nov. 3, 2011 (US).

* cited by examiner

ANTIMICROBIAL DEVICE FOR WOUND CARE

RELATED APPLICATIONS

Not Applicable.

BACKGROUND OF THE INVENTION

1. Field of the Invention

The present invention relates generally to the field of wound care, and more specifically to a device for eliminating or reducing the presence of viable microorganisms at the site of a wound or on the surface of an instrument inserted through a wound. The invention also relates to improving healing of tissues at or near a wound site through increased oxygenation of the tissues at the local area, and changing the gaseous concentration around the wound area such that it is not conducive to the growth of a pathogenic organism. Oxygen levels in the local area may be increased without the need for expensive hyperbaric chambers.

2. Background

Infection at the site of a wound is always a serious concern for health care providers, whether due to microorganisms exposed to the patient outside of the healthcare facility or within the healthcare facility, where microorganisms are prevalent. The 'wound' may be the result of accident or other trauma, or may be intentional, such as the wound that results from the insertion of a hemodialysis catheter or other instrument into the patient's body. Any puncturing of the epidermis produces a wound that may be susceptible to infection.

A device for reducing the risk of infection at the site of a wound is needed.

SUMMARY OF THE INVENTION

The present invention provides a device for protecting against microbial infection. The device includes a cover having a concave interior surface and a convex exterior surface. The device further includes an adhesive flange for affixing the cover to a patient's skin. A membrane extends across at least a portion of the interior surface of the cover for retaining an antimicrobial compound between the membrane and the interior surface of the cover. The membrane is permeable to the antimicrobial compound so that the antimicrobial compound is released through the membrane over time.

In another aspect of the invention, the device includes an inlet extending through the cover and the membrane. The inlet defines a central opening for introducing an antimicrobial compound into the space between the membrane and cover.

In another aspect of the invention, the device includes an outlet extending between the membrane and the skin of the patient. The outlet defines a central passage for aspiration of the space between the membrane and the patient's skin.

In another aspect of the invention, the membrane is a tubular membrane extending along an interior perimeter of the cover.

In another aspect of the invention, the device includes a drainage structure fixedly attached to the interior surface of the cover. The drainage structure has a lower surface having at least one opening therein, so that material between the membrane and the patient's skin moves through the opening and into the drainage structure.

In another aspect of the invention, the membrane is configured to retain the antimicrobial compound under pressure.

Another aspect of the invention provides a device for protecting against antimicrobial infection that includes an inflatable reservoir, a first inlet tube in fluid communication with the inflatable reservoir, and a semipermeable conduit in fluid communication with the semipermeable membrane. A cover extends over the inflatable reservoir and semipermeable conduit and defines an opening for the inlet tube. When an antimicrobial agent is introduced into the inflatable reservoir, at least a portion of the antimicrobial agent flows into the conduit. The antimicrobial agent is able to flow through the semipermeable conduit to an interior space of the device.

In another aspect of the invention, the inflatable reservoir is configured to retain an antimicrobial agent under pressure.

Another aspect of the invention provide an outlet tube extending through the cover and into the interior space defined by the device, the outlet tube allowing aspiration of the contents of the interior space defined by the device.

In another aspect of the invention, the inflatable reservoir comprises a semipermeable membrane.

In another aspect of the invention, the device includes a second inflatable reservoir and a second semipermeable conduit in fluid communication with the second inflatable reservoir. When a second antimicrobial agent is introduced into the second inflatable membrane, at least a portion of the second antimicrobial agent flows into the second semipermeable conduit and the second antimicrobial agent is able to pass through the second semipermeable conduit into the interior space of the device.

In another aspect of the invention, the semipermeable conduit is malleable and may be shaped by the user to define the perimeter of a wound being treated.

Another aspect of the invention relates to the customization of the shape of the device around the wound by scanning the site of the wound with a 3D scanner. The flange/device may then be customized to precisely fit around the site so there is minimal or no leakage of the contents. The flange can be made of PLA/ABS plastic and 3D printer may be used to custom print the device directly at the point of use. Open source 3D programming may be used to scan the wound site as well as to customize the creation of the device. Use of such a custom version of the device may add comfort and utility to the device.

The antimicrobial compound used with the present device may be a gas, a liquid, a gel, an oxidizing agent, or any other suitable agent.

The permeability of the membrane of the present device is such that a sustained, constant release of antimicrobial compounded is maintained over a desired treatment period.

Another aspect of the present invention may also include a cover, an adhesive flange, and a valve for introducing gas into the interior of the device or releasing gas from the interior of the device. Such an embodiment of the present device is airtight when affixed to a patient's skin via the adhesive flange so as to maintain as constant state within the interior of the device over a desired treatment period.

The constant state within the interior of the device may include any gas or combinations of gases, or may include a vacuum.

The device may further include an antimicrobial structure. Such an antimicrobial structure may be a heating element for maintaining a desired temperature of a liquid or gas within the device, an ultraviolet source, an ultrasound source, or combinations thereof.

DETAILED DESCRIPTION OF THE INVENTION

Certain terms used herein refer to the orientation of the present device, or to the top or bottom thereof. As used herein, the word top, and like words, refers to the exterior, convex surface of the cover of the present device. This holds true whether the device is oriented so that this surface extends upward, such as when the device is positioned atop a wound on a patient's skin, or when the device is positioned on the underside of a patient's skin. Likewise, the interior, concave surface of the cover of the present device may be referred to as the bottom of the device, regardless of the actual orientation of the device. Use of the words top and bottom, or any such directional terms, for other parts of the present device are to be interpreted in a manner consistent with the 'top' and 'bottom' of the cover, as defined above.

The term 'wound' is also used herein, and refers to any break in the integrity of the epidermis of a patient, whether that break is accidental, or is the result of an intentional break in the epidermis, such as for the insertion of a catheter or other instrument.

The term antimicrobial compound is used broadly herein to refer to any compound that achieves an antimicrobial effect in situ. Thus, the term may refer to compounds, such as antibiotics, that are directly antimicrobial in function, or to compounds such as hydrogen peroxide, which achieve an antimicrobial effect only by reaction with another compound (in the case of hydrogen peroxide, the enzyme catalase). Further, as defined herein, $O_2$ is considered an antimicrobial compound for purposes of the present invention, when present at sufficient concentration to have an antimicrobial effect. The form of the antimicrobial compound may include a liquid, gas, gel, or any other suitable form of compound.

Figure 1:
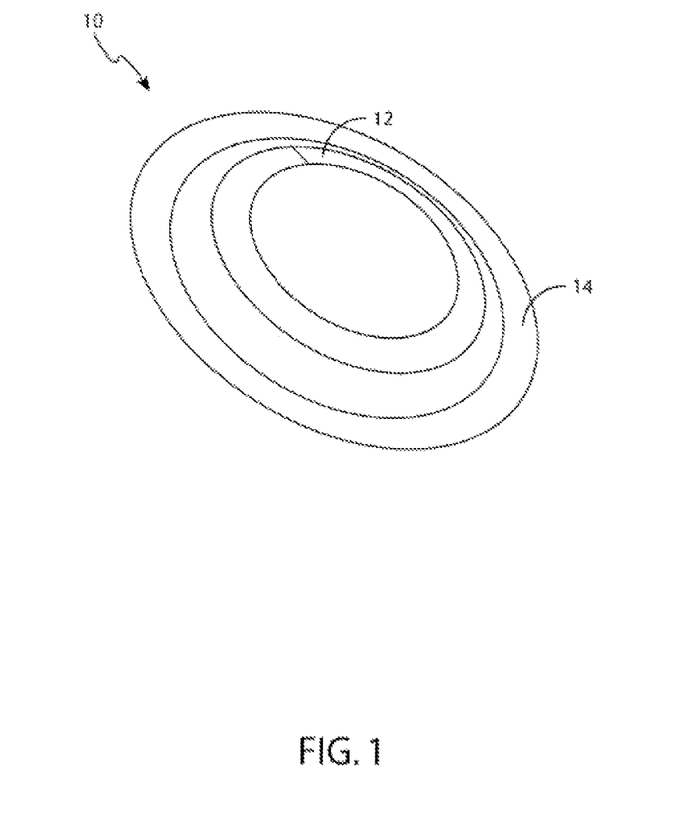
FIG. 1 is a top and side view of one embodiment of an antimicrobial wound care device of the present invention.

Turning now to the drawings, wherein like numerals indicate like parts, FIG. 1 is a top and side view of one embodiment of an antimicrobial device 10 of the present invention. In the embodiment of antimicrobial device 10 shown in FIG. 1, a cover 12 is provided, cover 12 having an adhesive flange 14 extending around the perimeter thereof. Cover 12 is preferably constructed of a rigid or semi-rigid material, though any suitable material may be used in its construction. A dermal surface membrane 16 is provided within cover 12, as best seen in FIGS. 2 and 3, which depict various embodiments of a wound care device.

Dermal surface membrane 16 is constructed of a permeable material, and may be selectively permeable, semi-permeable, or may allow any material therein to pass into the space between cover 12 and a wound site. An inlet 13 may pass through cover 12, as shown in FIG. 2, and may be in fluid communication with the interior of dermal surface membrane 16, the inlet 13 allowing for introduction of various antimicrobial materials into dermal surface membrane 16. In the embodiment shown in FIG. 3, cover 12 also includes one or more outlets 15 that can be used to aspirate the interior of cover 12, drawing fluid or other materials out of cover 12 and away from the wound site. In some embodiments of the invention, outlets 15 may simply extend through cover 12 into the interior space thereof. In other embodiments of the invention, cover 12 may include a drainage structure 17, such as that shown in FIG. 3, having a plurality of openings therein, such that fluid or other material within the interior of cover 12 passes through the openings and into drainage structure 17. In embodiments wherein both outlets 15 and drainage structure 17 are used, outlets 15 may be in fluid communication with the interior of drainage structure 17 and can be used to aspirate material from the interior thereof. Outlets 15 are preferably accessible from the exterior of the device for aspiration.

Figure 2:
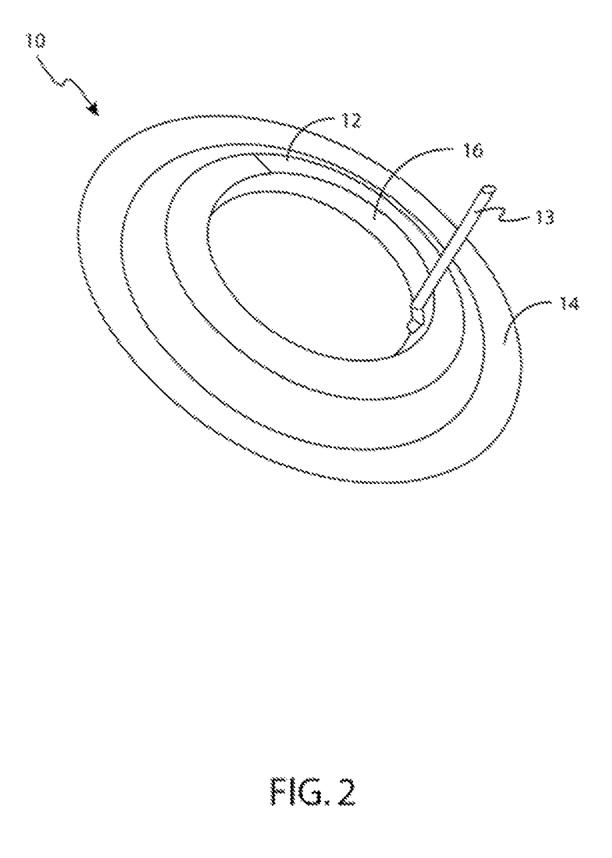
FIG. 2 is a perspective view of another embodiment of an antimicrobial wound care device of the present invention.
Figure 3:
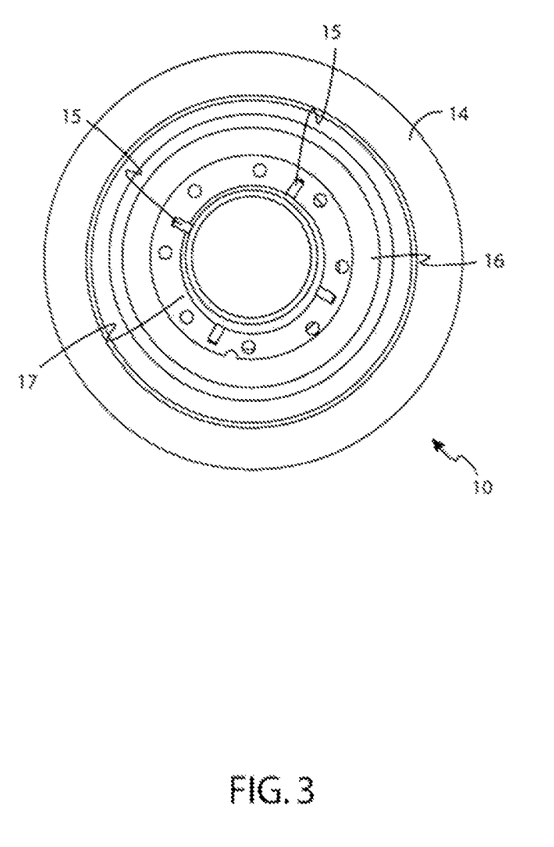
FIG. 3 is a bottom view of one embodiment of an antimicrobial wound care device of the present invention.

Dermal surface membrane 16 may be provided as a single layer of membrane extending across a portion of the interior of cover 12, or maybe provided, as shown in FIGS. 2 and 3, as a tubular structure that extends along an inner circumference of cover 12. Inlet 13 is used to introduce an antimicrobial compound into dermal surface membrane 16, the membrane allowing the compound to move into the interior space of cover 12 over time, thereby coming in contact with the wound site. Any suitable antimicrobial compound, or combination of compounds, may be introduced into dermal surface membrane 16. For example, antibiotics may be used to kill bacteria at or near the wound site. Likewise, hydrogen peroxide may be used, the hydrogen peroxide reacting with the enzyme catalase present at the wound site to generate oxygen levels lethal to microorganisms. In some embodiments of the invention, oxygen gas may be introduced into the membrane, or compounds that produce oxygen gas may be utilized. In such embodiments, a hyperbaric oxygen environment may be created within cover 12, aiding in the elimination of microorganisms and the healing of tissue at the wound site. It is contemplated that in such embodiments, the adhesive flange forms an airtight seal against the skin of the patient, and that device 10 is also constructed to be airtight. Inlets and outlets may include valves, seals, or other structures to ensure the device is airtight, as described further below. Such embodiments of the device may also be used to maintain a vacuum within the confines of the device, at the site of a patient's wound.

In the embodiment of antimicrobial device 10 shown in FIGS. 1 through 3, for example, an adhesive flange 14 is provided to allow device 10 to adhere to the skin of a patient. The adhesive seal provided by adhesive flange 14 prevents the antimicrobial compounds introduced into cover 12 from leaking out of the device. Adhesives suitable for use in adhering a device such as antimicrobial device 10 to a patient's skin are well known in the art. The adhesive may be applied to the bottom surface of adhesive flange 14, for example, and may be covered with a peelable strip to protect the adhesive until the device is ready for use. Flange 14 and cover 12 are flexible enough to allow flange 14 to conform to the skin of a patient at the site where the wound care device 10 is used.

Outlets 15 and inlet 13 are sealed when not in use for aspiration or introduction of a compound into dermal surface membrane 16. Inlet 13 may be structured such that it is unidirectional, such as via a one-way valve or other structure, so that material introduced into dermal surface membrane 16 is unable to leak out through inlet 13. Alternatively, inlet 13 may be provided with a cap. Outlets 15 may be capped or may be sealed in such that manner that they remain closed unless a force, such as that generated by aspiration with a vacuum, forces material through the seal and allows the material to exit cover 12.

FIG. 3 shows a bottom view of antimicrobial device 10. Outlets 15 are visible, as is drainage structure 17. Dermal surface membrane 16 is shown, as well as adhesive flange 14, which serves to hold the device firm against the skin of a patient.

Figure 4:
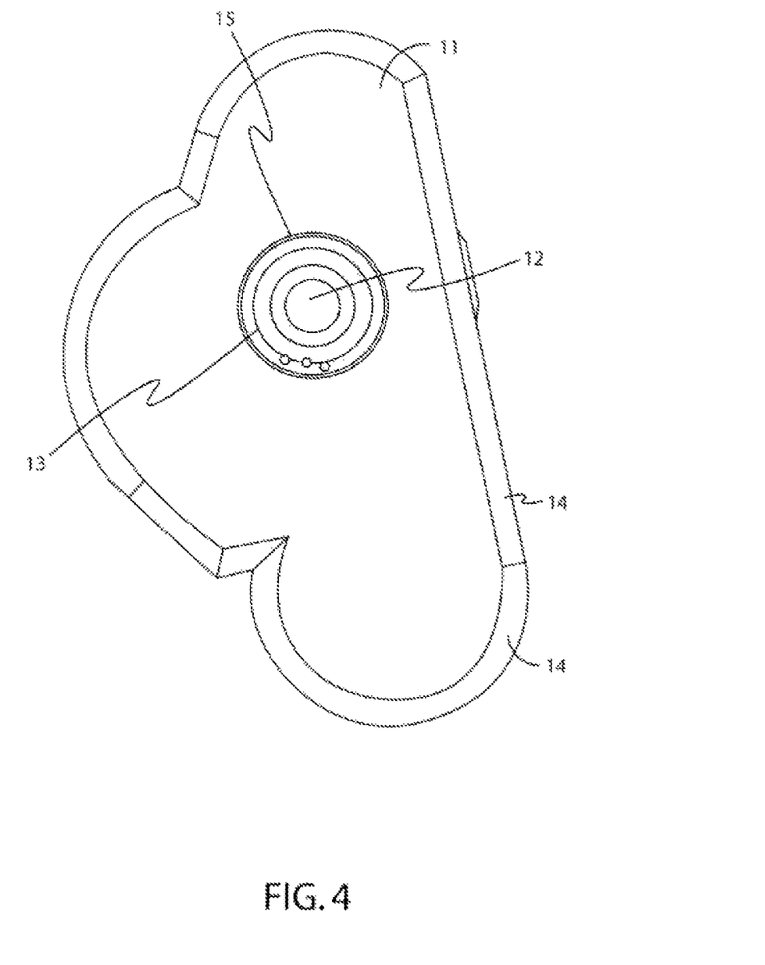
FIG. 4 is a bottom elevation view of another embodiment of an antimicrobial wound care device of the present invention.

FIG. 4 shows a bottom view of one embodiment of a device of the present invention covering a wider wound or skin area than the devices shown in FIGS. 1 through 3. Cover 12 is shown here as a first cover, as is the dermal surface membrane, which may contact the skin at the specific point of a wound, or at a portion of the wound. A wider second cover 11 is shown, which extends over a greater portion of the patient's skin and includes one or more adhesive flanges 14 around the perimeter thereof. The embodiment of the present device shown in FIG. 4 may be used to provide concentrated antimicrobial activity at the site of a wound (such as, for example, the entry point for a catheter), and also to provide a wider area of antimicrobial activity around the point of the wound, to further reduce the probability of infection of the wound. The size and shape of second cover 11 may be varied such that the device is suitable for use at a variety of locations on a patient's body, and to cover a variety of sizes and shapes of wound.

Figure 5:
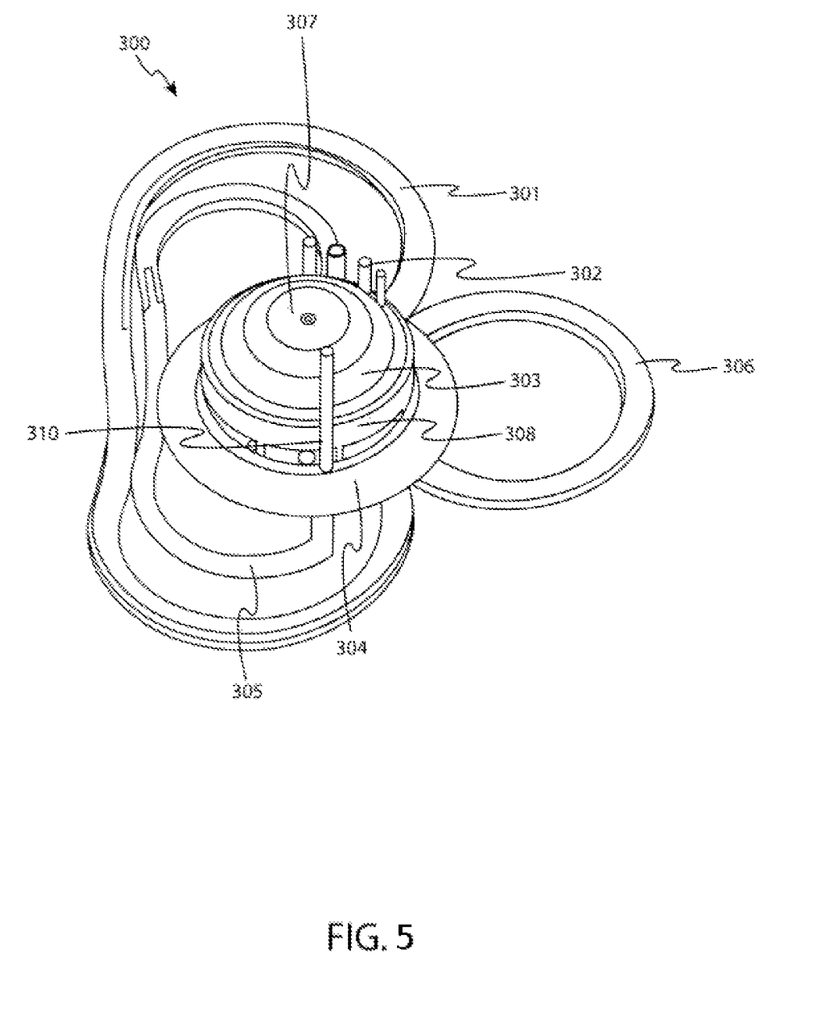
FIG. 5 is a perspective view of one alternative embodiment of an antimicrobial wound care device constructed in accordance with the teachings of the present invention.

FIG. 5 depicts an embodiment of a wound-care device constructed in accordance with the teachings of the present invention. Conduit 301 forms a perimeter of device 300, and may be shaped to conform to the size and shape of a wound being treated. Conduit 301 is preferably constructed from a semi-permeable membrane, or from a plastic or polymer material. An antimicrobial compound or agent is provided within conduit 301, and the antimicrobial agent leaks, at a controlled rate, out of conduit 301 and into the area of the wound being treated as defined by device 300. Any suitable antimicrobial agent may be used with device 300, including liquids, gasses, gel-like substances, and so on. Further, although a semi-permeable membrane or a polymer compound with pores to allow passage of the antimicrobial compound may be used in the construction of conduit 301, it is contemplated that any suitable structure for allowing flow-over-time of the antimicrobial agent out of conduit 301 may be utilized.

An antimicrobial agent may be delivered to conduit 301 through port 302, for example. Port 302 may be used to provide an initial amount of antimicrobial agent once wound care device 300 is put in place at the site of a wound, or may be used to introduce additional antimicrobial agent into conduit 301 once the antimicrobial agent is depleted or levels have grown low. Port 302 preferably includes a one-way valve to prevent the antimicrobial agent from exiting wound care device 300 via that port.

Additional conduits 305 and 306 may also be provided, either to extend over or around additional areas requiring care or treatment, or to provide additional delivery of antimicrobial agents within wound care device 300. The same antimicrobial agent may be used, in the same concentration, in each of the conduits, or differing concentrations or agents may be provided in different conduits of device 300.

The embodiment of device 300 shown in FIG. 5 also includes an inflatable reservoir 303 that contains an antimicrobial agent stored under pressure. The pressure used is preferably sufficient to enable a constant flow of antimicrobial agent from inflatable reservoir 303 to the surface of the wound being treated. Torus-shaped semipermeable membrane 304 is also provided, and is in fluid communication with any or all of conduits 301, 305, and 306. The antimicrobial agents used in device 300 may be introduced only into reservoir 303, and the remaining conduits or reservoirs may be in fluid communication therewith, such that the antimicrobial agent introduced into reservoir 303, and contained therein under pressure, is distributed to the other conduits or membranes from reservoir 303 as a result of the pressure acting on the antimicrobial agent within reservoir 303. Also, in some embodiments of the device, semipermeable membrane 304 may be replaced with a reservoir similar to reservoir 303. Membrane 304 may, in that case, be in fluid communication with a first set of membranes or conduits of device 300, while reservoir 303 is in communication with a second set of conduits or membranes. A first antimicrobial agent may be introduced into membrane 304 and a second antimicrobial agent may be introduced into reservoir 303, with the two antimicrobial agents being distributed along separate conduits or membranes due to pressure acting on the antimicrobial agents within reservoir 303 and membrane 304. Thus, a dual, complementary action between two antimicrobial agents may be achieved.

An overflow reservoir 308 is provided, with access for suctioning, so that excess fluid from the surface of the wound, or excess antimicrobial agent, may be removed from the site of the wound.

Figure 6:
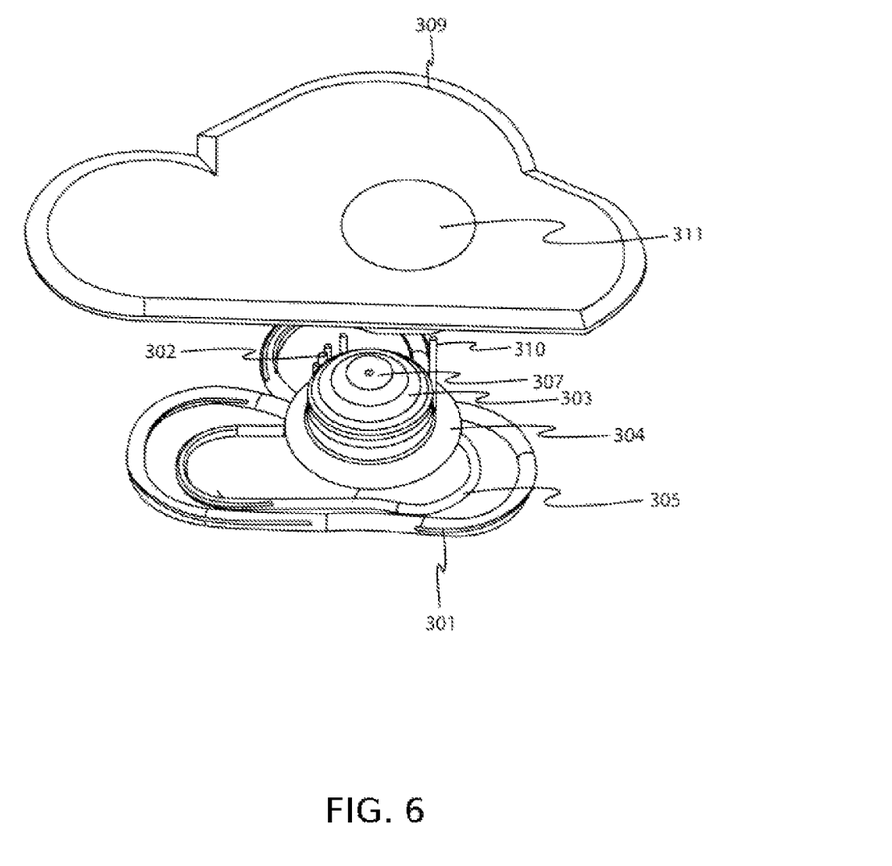
FIG. 6 is a perspective view of the embodiment of an antimicrobial wound care device shown in FIG. 5, with a cover for the wound care device shown positioned thereover.

FIG. 6 shows wound care device 300 from a different perspective, with cover 309 included in the figure. Cover 309 can be customized in terms of size and shape as necessary or desirable according to the size and shape of the wound being treated. Cover 309 includes a flange extending along the perimeter thereof, and this flange preferably includes an adhesive so that cover 309 can be attached to the skin of the patient receiving treatment. Opening 311 in cover 309 allows cover 309 to be slipped over wound care device 300. Cap 307 preferably fits tightly at the site of opening 311.

Figure 7:
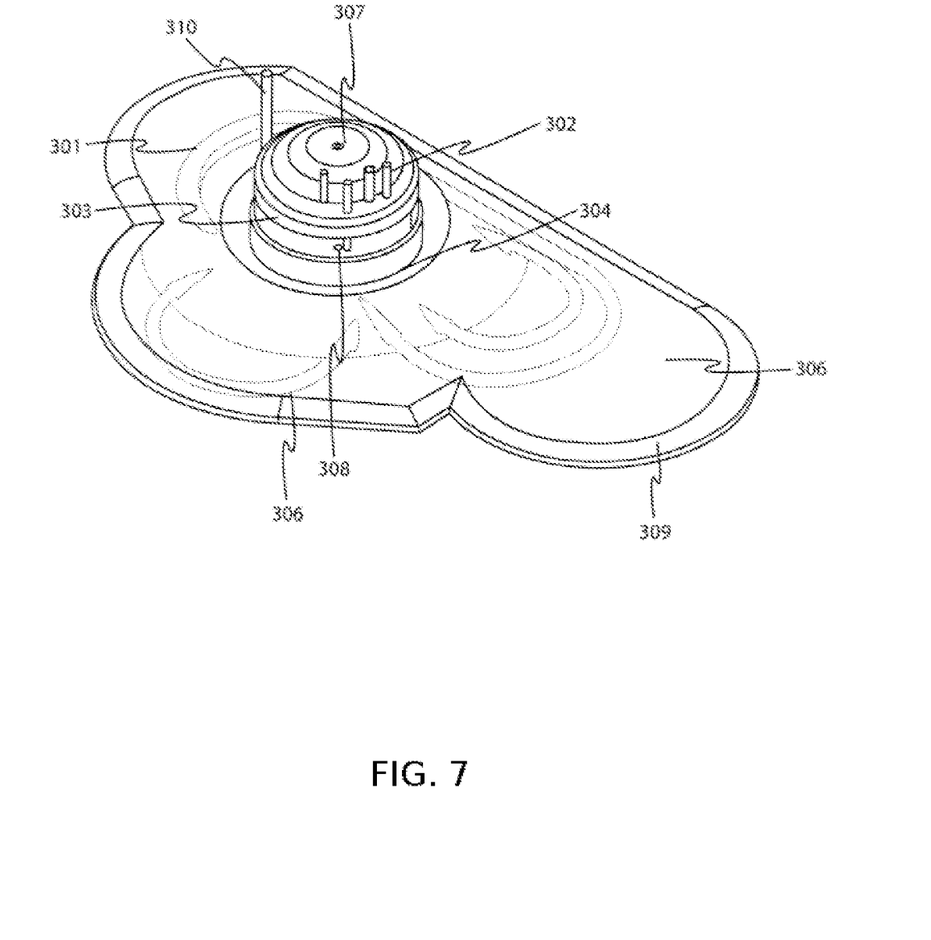
FIG. 7 is a perspective view of the antimicrobial wound care device of FIG. 6, with the cover in place thereon.

FIG. 7 shows an assembled wound care device 300 as described above, with various conduits and interior structure of wound care device 300 illustrated with dashed lines.

In the various embodiments of the present device described above, structural antimicrobial elements may also be provided. These antimicrobial structures may be any that serve to generate an antimicrobial effect such as, for example, one or more heating elements that may be used to raise the internal temperature of the device to a level that will not sustain microbial growth, or may include an ultraviolet or ultrasound source that can serve to kill at least a portion of the microorganisms at the wound site. These structure elements are within the device, underneath the cover, and may be provided in any suitable location. Heating elements may be attached to the cover itself, or to various conduits or other structure, and may be used to heat gases or fluids within the wound care device, and to maintain those gases or fluids at a desired temperature.

In each of the various embodiments of the present invention, the device serves to maintain a steady state of antimicrobial activity. This is in marked contrast to the use, for example, of antimicrobial ointments in combination with bandages and the like. In such circumstances, an initial high level of antimicrobial activity is provided, however that initial peak of antimicrobial activity drops substantially over a relatively short period of time. The present device creates a steady state of antimicrobial activity so that there is no "peak" followed by an undesirable drop-off in antimicrobial activity. This not only decreases or inhibits antimicrobial growth, but also facilitates healing at the site of the wound and reduces the risk of antimicrobial resistance emerging among the population of pathogenic microorganisms at the wound site.

In some embodiments of the invention, various components of the invention may be constructed of a flexible or malleable material that may be shaped by the end user to a desired conformation. This is particularly useful in terms of shaping one or more of the conduits of the present invention to fully surround a wound, or to conform as best as possible to the shape thereof, or in shaping the device as a whole, such that the flange takes on a customized conformation for attachment to the skin of the patient. Such shaping may take into account the area on the patient's body where the device is to be placed, the contours of the patient's skin, and so on.

In other embodiments of the invention, the present device may be custom-made at the point of use such that it has the necessary or desired dimensions for a given wound treatment. A digital camera, scanner, or other such device may be utilized to scan or photograph the area of the wound desired to be treated. Once the necessary data is acquired, a 3D printer may be used to "print" various components of the device, such as, for example, the flange, cover, and the like so that it conforms to the shape and size of the wound being treated. In some embodiments, wherein the various membranes or conduits described above are replaced with structures having physical openings capable of being reproduced with a 3D printer, the entire device may be printed in such a manner.

Further Principles and Alternatives

It is to be understood that the invention disclosed herein is suitable for use in a variety of manners, incorporating various principles of wound management. For example, when wound care calls for the use of antibiotic treatments, the present device may be utilized to maintain deliver of antibiotics to the wound site.

Further, the present device may assist in wound debridement, which is vital to treatment of wounds having contamination or other material therein. The inlet ports of the various embodiments of the invention may be used to introduce fluids for use in debridement, the fluids and accompanying contaminants being aspirated from the wounds via the ports provided for that purpose.

Likewise, irrigation of a wound may be provided using the present device. For example, a warm, isotonic saline solution may be introduced to the wound site using the present device, and irrigation fluid may matter loosened from the wound site may be aspirated in the manner described above.

In some wound care applications, enzymatic debridement is used, wherein exogenous enzyme is applied to the wound site for debridement or other functionality. It is contemplated that the introduction of exogenous enzyme solutions to a wound site may be accomplished via the present invention, and the aspiration of such material, when necessary, may also be accomplished as described above.

Other topical treatments may also be applied to, and maintained at, a wound site using the present device. These include growth factors important in wound healing, antiseptic agents, foam dressings, and the like.

The various components of the embodiments described above and shown in the drawings may be connected in any suitable manner. Some components, such as conduits and membranes, are in fluid communication, and may be provided as single, contiguous portions of material or may be multiple portions of material attached by adhesives, heat, or other known processed. Components not in fluid communication may likewise be manufactured as single pieces, attached by adhesives, heat processes, and so on. It is contemplated that various methods or processes for attaching the components of the present device are well known in the art.

The foregoing descriptive and accompanying illustrations are intended to be exemplary of the principles of the present invention. Various modifications to the description provided herein will be readily apparent to one of ordinary skill in the art upon reading this disclosure, and it is contemplated that such modifications are within the spirit and scope of the present invention.

Having thus described the preferred embodiment of the invention, what is claimed as new and desired to be protected by Letters Patent includes the following:

1. A device for protecting against microbial infection, the device comprising:
   a cover having a concave interior surface;
   an adhesive flange for affixing the cover to a patient's skin;
   a membrane extending along at least a portion of the interior surface of the cover, wherein the membrane is a torus-shaped enclosure capable of retaining an antimicrobial compound therein;
   an inlet extending through said cover and in fluid communication with an interior space of said device, wherein the inlet is configured to receive an antimicrobial compound from an antimicrobial compound source; and
   an outlet extending through said cover and in fluid communication with a second interior space of said device, wherein the outlet is configured to direct fluid away from said wound being treated,
   wherein the membrane is permeable to the antimicrobial compound such that the antimicrobial compound is released therefrom over time.

2. The device according to claim 1, further comprising:
   an antimicrobial source disposed beneath the cover of said device.

3. The device according to claim 1, further comprising a drainage structure fixedly attached to the interior surface of the cover, the drainage structure comprising a lower surface defining a space between the lower surface and the wound being treated by said device when the device is in operative position covering the wound, the lower surface further defining at least one opening therein such that material between the lower surface of the drainage structure and said wound moves through the at least one opening in the lower surface of the drainage structure to a space within the drainage structure.

4. The device according to claim 1, wherein said membrane is configured to retain the antimicrobial compound under pressure.

5. The device according to claim 1, wherein said cover is formed in a shape defining a perimeter of a wound being treated by a method comprising the steps of:

a) acquiring a digital image of the wound to be treated; and
b) printing said cover utilizing 3-D printing technology.

6. The device according to claim 1, further comprising an antimicrobial structure underneath the cover of said device, the antimicrobial structure selected from the group consisting of:
   a heating element for maintaining a desired temperature of a liquid or a gas within said device, an ultraviolet source, an ultrasound source, and combinations thereof.

7. The device according to claim 1, further comprising an ultraviolet source disposed underneath the cover of said device.

8. The device according to claim 1, wherein said inlet is operable to alternate between a sealed configuration and an unsealed configuration.

9. The device according to claim 1, wherein said outlet is operable to alternate between a sealed configuration and an unsealed configuration.

\* \* \* \* \*